United States Patent [19]

Carle et al.

[11] Patent Number: 4,538,066
[45] Date of Patent: Aug. 27, 1985

[54] MODULATED VOLTAGE METASTABLE IONIZATION DETECTOR

[75] Inventors: Glenn C. Carle, Sunnyvale; Daniel R. Kojiro, San Jose; Donald E. Humphry, Cupertino, all of Calif.

[73] Assignee: The United States of America as represented by the Administrator of the National Aeronautics and Space Administration, Washington, D.C.

[21] Appl. No.: 582,643

[22] Filed: Feb. 22, 1984

[51] Int. Cl.³ ............................................. H01J 47/02
[52] U.S. Cl. .................................... 250/374; 250/379
[58] Field of Search ................ 250/374, 375, 379, 380

[56] References Cited

U.S. PATENT DOCUMENTS

| | | |
|---|---|---|
| 3,358,140 | 12/1967 | Curran et al. |
| 3,379,968 | 4/1968 | Yamane |
| 3,445,757 | 5/1969 | Krucoff |
| 3,559,049 | 1/1971 | Lieberman et al. |
| 3,569,825 | 3/1971 | Lilienfeld |
| 3,713,773 | 1/1973 | Fontijn et al. |
| 3,984,690 | 10/1976 | Marshall et al. ..................... 250/374 |
| 4,117,332 | 9/1978 | Felton et al. ........................ 250/374 |
| 4,345,154 | 8/1982 | Bainbridge ........................... 250/375 |

*Primary Examiner*—Janice A. Howell
*Attorney, Agent, or Firm*—Darrell G. Brekke; John R. Manning; Robert D. Marchant

[57] ABSTRACT

Metastable ionization detectors used for chromatographic analysis usually employ a fixed high voltage for the ionization potential. For this reason, the operating range is limited to about three orders of magnitude. By use of the technique disclosed in the instant invention, operating ranges of about nine orders of magnitude are obtained.

The output current from a metastable ionization detector (MID) is applied to a modulation voltage circuit. An adjustment is made to balance out the background current, and an output current, above background, is applied to an input of a strip chart recorder. For low level concentrations, i.e., low detected output current, the ionization potential will be at a maximum and the metastable ionization detector will operate at its most sensitive level. When the detected current from the metastable ionization detector increases above a predetermined threshold level, a voltage control circuit is activated which turns on a high voltage transistor which acts to reduce the ionization potential. The ionization potential applied to the metastable ionization detector is then varied so as to maintain the detected signal level constant. The variation in ionization potential is now related to the concentration of the constituent and a representative amplitude is applied to another input of said strip chart recorder.

13 Claims, 3 Drawing Figures

Fig_1

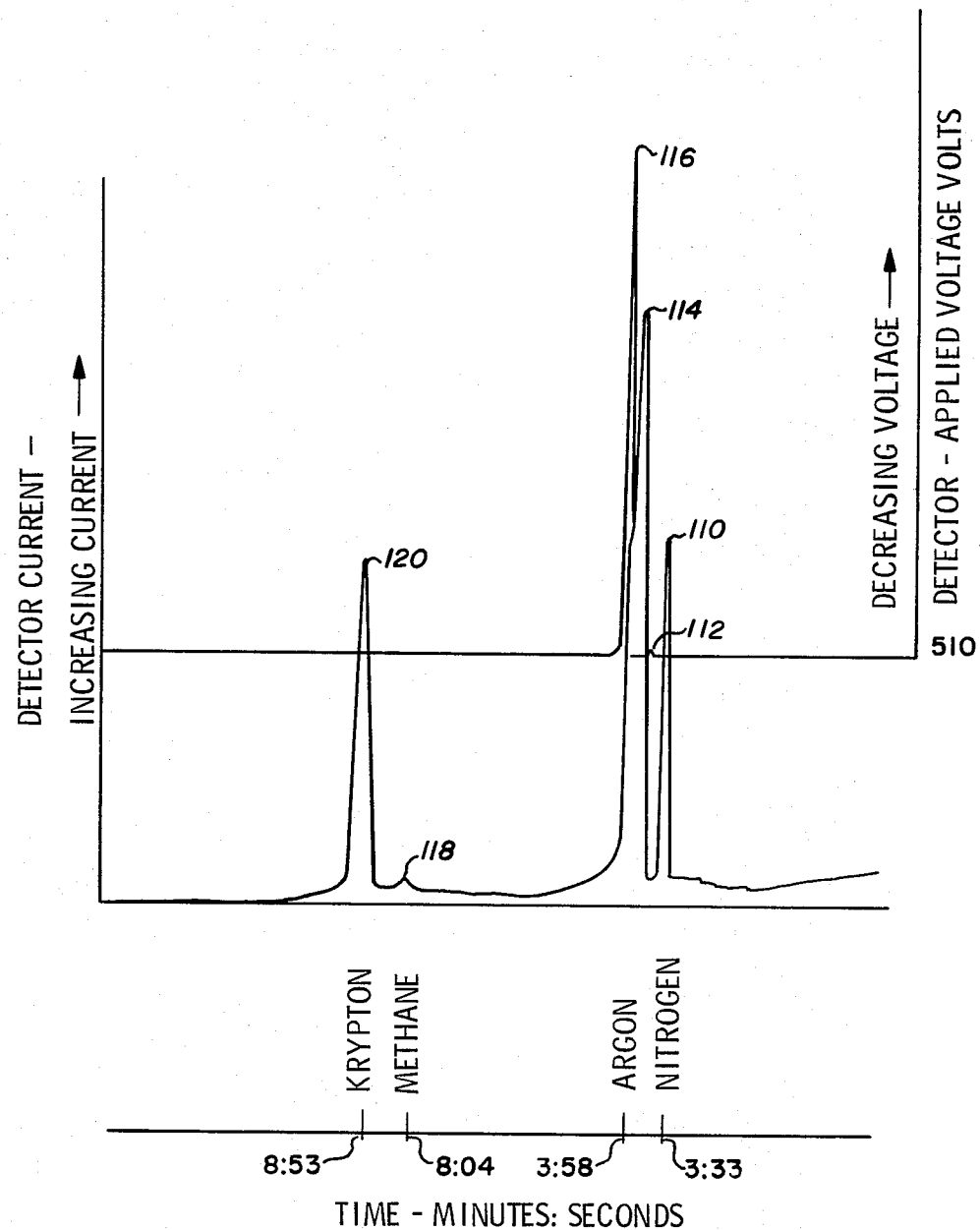
Fig_3

MODULATED VOLTAGE METASTABLE IONIZATION DETECTOR

ORIGIN OF THE INVENTION

The invention described herein was made by employees of the United States Government and may be manufactured and used by or for the government for governmental purposes without the payment of any royalties thereon or therefor.

TECHNICAL FIELD

This invention relates to gas chromatography which employs ionization detection for quantitative measurement of sample concentrations and, more particularly, to method and apparatus for automatically extending the range, of an ionization detector so that quantitative measurements as low as 1 part per billon (ppb) and as high as 100% may be obtained.

BACKGROUND ART

Gas chromatography has been known for many years and is used principally as an analytical technique for the determination of volatile compounds (gases and liquids) with boiling points up to approximately 500° C. It is a separation technique involving the passage of a gaseous moving phase through a column containing a fixed phase. The separations are achieved by selective retardation exerted by the fixed phase because of differences in partition coefficients for gas-liquid chromatography. Of the three ways in which separation may be achieved, elution development is most commonly employed. Elution development requires the use only of a small sample which is injected at the inlet of a column. This sample is eluted by a constant flowing stream of a carrier gas which is generally inert (non-soluble and non-adsorbed), such as helium, nitrogen, or hydrogen. Because of the separation, the constituents of the sample substance appear as bands which travel through the column each at its own specific rate under the conditions of the test. Where the bands are separated, pure carrier gas emerges from the column between the different bands. Separation of the constituents or components of the sample is a first step in the analysis. The next step is detection of the presence of the constituents and their measurement.

Two principal methods are available for detecting and measuring the components in the effluent gas. These are classified as integral or differential types depending upon whether the effect produced on the device is measured additively or instantaneously. Differential detection is most widely used and techniques have been developed for analysis of thermal conductivity, gas density differences, and ionization properties. The most sensitive detectors are of the ionization type. Typically, the detector measures some physical property of the gases eluting from the column. When the composition of the gas eluting from the column changes, indicating that some sample component is eluting, the physical property being measured changes and this is sensed by the detector.

The operation of ionization detectors often is based upon the principle that a change in electrical conductance of an effluent gas is brought about by ionization of the sample component. One way in which ionization may be accomplished is to use a hydrogen flame ionization detector in which the ions are produced as the component burns. Another detector, the metastable ionization detector (MID) utilizes the Penning Effect of rare gases to detect sample components. Carrier gas molecules, usually helium, are used as the carrier, and these molecules are exposed to an electric field as well as to beta radiation from a radioactive source. This combination raises the carrier gas molecules to a metastable state with an ionization potential for helium of 19.8EV. As a result, all constituents having a lower ionization potential will be ionized giving rise to a positive signal output. The resulting electrons and ions are collected by the detector electrodes and typically measured by an electrometer coupled thereto. The metastable ionization detector (MID) provides an effective means by which the constituents of a sample may be detected, but it has drawbacks.

Although the MID is a very sensitive detector, it has a limited response range, i.e., at a given voltage setting, it can only quantitatively respond to sample concentrations over a limited range. At maximum sensitivity, the MID will detect constituents of a sample in the parts per billion (ppb) range, but will saturate for concentrations in the order of 10 parts per million (ppm). Saturation occurs when so much of a sample is ionized within the MID that the detector is overloaded and compensates for this overload by an arc discharge. Because arcing within the MID can damage the radioactive foil component of the detector, as well as create pits and holes in the MID walls and electrodes, care must be exercised to avoid the presence of such high concentrations. One technique by which arcing may be suppressed is to install a limiting resistor in the high voltage lead to one of the electrodes. By so doing, no meaningful quantitative data can be obtained when the detector is saturated.

One approach to a solution to this problem is disclosed in U.S. Pat. No. 4,345,154, issued Aug. 17, 1982 by Agustus S. Bainbridge, entitled "BIAS-COMPENSATED, IONIZATION SENSOR FOR GASEOUS MEDIA AND METHOD FOR ATTAINING PROPER BIAS FOR SAME", which discloses a technique for determining the most effective bias voltage and pre-selected resistance to be provided by the biasing means. Thus, the patent discloses a method for biasing an ionization sensor so as to minimize the effect of the gas flow rate change on the output signal from the detector. The bias voltage is empirically determined by varying the flow rate and observing the output signal changes for different values of bias voltage. Once the value of the optimum bias voltage has been determined, this value is then applied as a fixed bias to the detector. In contrast, the present invention discloses a technique for significantly extending the dynamic range of a metastable ionization detector by automatically and continuously varying the gain of the detector as a function of its own output signal.

DISCLOSURE OF THE INVENTION

A problem with prior art gas chromatographic devices which employ metastable ionization detection is that the range over which they may be effective is about three orders of magnitude. Although the technique is particularly useful in trace analysis, i.e., for measurements in the parts per billion (ppb) range, where a range under test also contains high concentrations of a constituent, the prior art metastable ionization detectors would be unable to provide quantitative results in one analysis. For example, if the sample contains concentrations ranging over four orders of magnitude, say from 10 ppb to 100 ppm, accurate quantitative results could not be obtained in one analysis.

In the present invention, the detector output is applied to an electronic circuit that modulates the high voltage (ionization potential) applied to the parallel plate electrodes of the detector. For samples having a low concentration, the ionization potential is at a maximum, and the quantitative analysis is based upon the variations in detector output current. Once the detector output current reaches a predetermined threshold level, the amplitude of the ionization potential is modulated so as to maintain the detector output current at said threshold level. The quantitative analysis for higher concentrations is then related to the variations in amplitude of the ionization potential.

IN THE DRAWING

FIG. 3 is a chromatogram which illustrates the increased range of operation obtained using the teaching of this invention.

DETAILED DESCRIPTION OF THE PREFERRED EMBODIMENT

Figure 1:
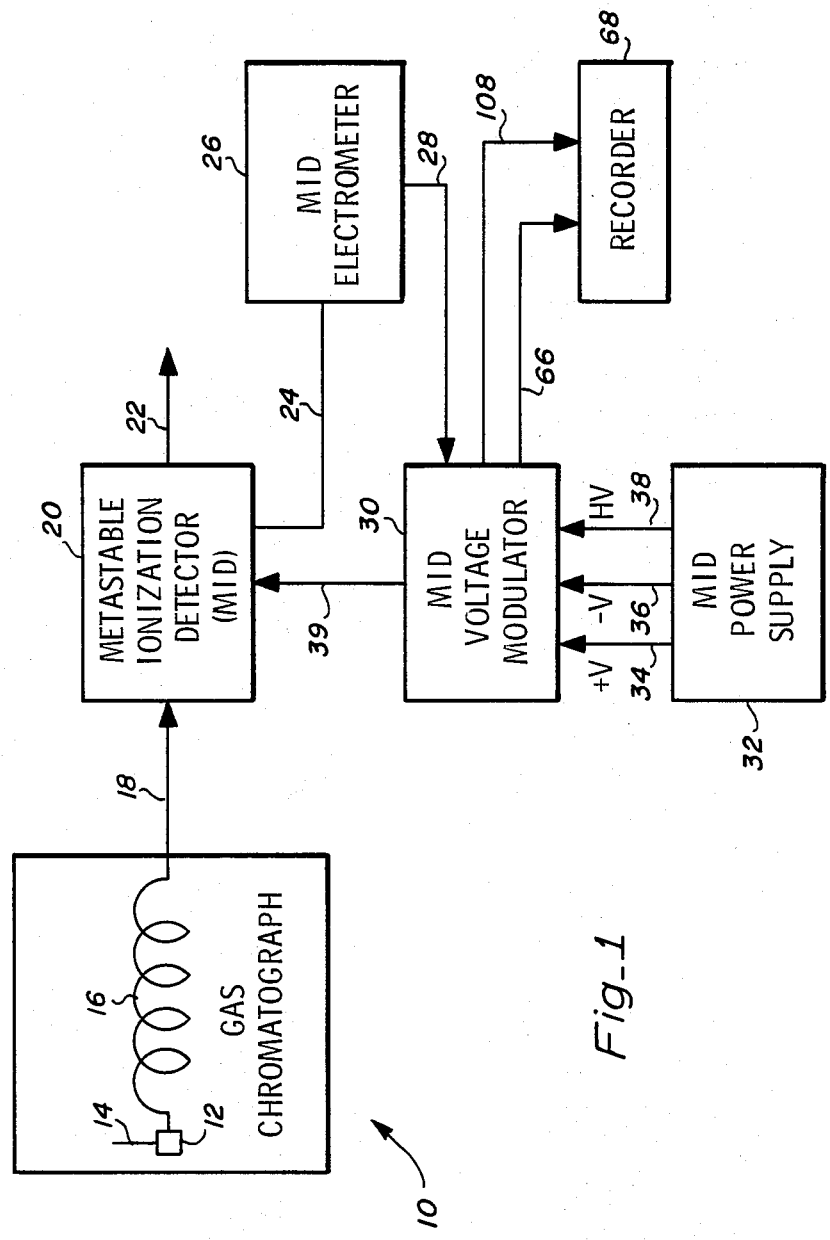
FIG. 1 is a block diagram illustrating a gas chromatagraphic system in which a metastable ionization detector (20) is used in conjunction with a voltage modulator (30) of the instant invention.

Referring now to FIG. 1, a gas chromatograph 10 includes a carrier gas inlet port 12 and a sample injection port 14 at the front end of a coiled column 16. Elution development is employed to obtain separation of the constituents of the sample, whereby these constituents are separated into bands by selective retardation exerted in the fixed phase because of differences in partition coefficients. A section of tubing 18 allows interconnection between the coiled column 16 and the metastable ionization detector (MID) 20 in which the detection of the presence of the constituents is obtained. The gas then passes through vent tube 22 to the outside atmosphere.

In order to obtain an effective measurement of a detected constituent, an electrometer 26 is employed. The electrometer 26 measures the potential difference between the electrically charged surfaces of the electrodes in the metastable ionization detector and derives a useful differential output current that is applied to an input of voltage modulator 30 via path 28. A MID power supply 32 provides the high voltage (HV) along path 38 to the high voltage input of voltage modulator 30 which, in turn, provides the ionization potential along path 39 to the metastable ionization detector 20. As will be explained in more detail hereinafter, the high voltage applied via path 39 is a constant high potential for low sample concentrations below a preset level. In this case, the constituent concentration is related to the variation in current. For constituent concentrations above the preset level, the MID output current is held substantially constant, and the constituent concentration is related to the variation in ionization potential. The sample characteristics are plotted as amplitude versus time using a strip chart recorder 68. Such recorders are well known.

Figure 2:
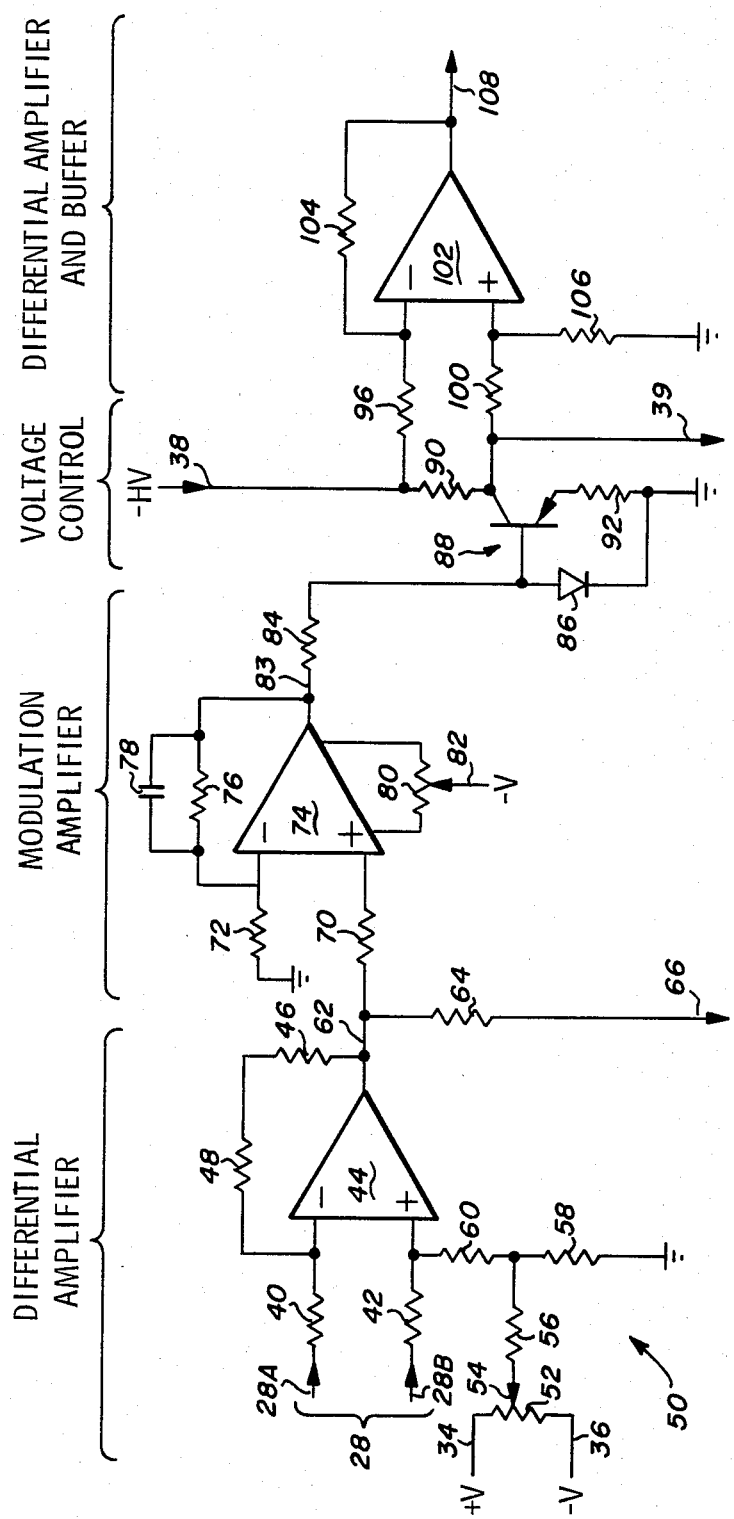
FIG. 2 is a schematic diagram illustrating a preferred embodiment of the voltage modulator of the instant invention.

Turning now to FIG. 2, it may be seen that the differential signal from electrometer 26 is applied to the balanced input circuit of differential amplifier 44 via leads 28A and 28B and equal valued resistors 40 and 42. As is well known, the beta particles which emanate from the tritium foil have a relatively low probability of collision with the orbital electrons of the carrier gas molecules, normally hydrogen or helium, i.e., the cross section for ionization of the hydrogen or helium is very low. The electrons generated by these collisions are instantly collected and produce a small background current. Thus a small background current will normally appear at the output of differential amplifier 44 on path 62.

Because the presence of this background current is undesirable, an offset control circuit 50 is provided to compensate for this background current. Adjustable resistor 52 is connected to $+V$ and $-V$ voltage sources from power supply 32 via paths 34 and 36, respectively. Wiper 54 is connected via resistors 56 and 58 to ground to form a voltage divider network. The junction of resistors 56 and 58 is connected to one terminal end of resistor 60 whereas the other terminal is connected to the non-inverting input of differential amplifier 44. Feedback resistors 46 and 48 are selected to be equal, respectively, to resistors 58 and 60. Wiper 54 is moved on resistor 52 and set so that the strip chart on recorder 68 indicates a 0 reading when only carrier gas is passing through the gas chromatograph 10.

For low levels of gas concentration the ionization potential applied via path 39 to metastable ionization detector 20 is at a maximum, and the variation in detector output, which appears on path 62, is applied via resistor 64 to one input of recorder 68 via path 66. Resistor 64 is used so as to avoid capacitively loading the output of the differential amplifier. This capacitive effect is present because of the characteristic of the coaxial cable which is normally employed for connection between the electrometer and the recorder.

The detected current appearing on the path 62 is applied via resistor 70 to the non-inverting input of operational amplifier 74, and a like valued resistor 72 is connected between the inverting input and ground. Thus, amplifier 74 is connected for operation as a non-inverting single ended amplifier. An RC feedback network comprising resistor 76 and capacitor 78 is provided. Resistor 76 is selected in relation to the value of the input resistor to obtain the desired gain. By appropriate adjustment of a wiper 82 on resistor 80 a bias voltage is applied to operational amplifier 74. The bias voltage is adjusted so that the output of the amplifier 74 is slightly below the level to turn on high voltage transistor 88, when the current on path 62 is at or below the threshold. When enabled by current on path 62, amplifier 74 provides a DC output voltage on path 83.

This threshold may be adjusted to set the minimum and maximum values of constituent concentration and the setting will depend upon the quantitative values anticipated in a measurement. A voltmeter could be employed to set the bias voltage and could be included as a part of the circuit. Alternatively, test points could be provided for the measurement. It is necessary only to set the threshold so that the output of operational amplifier 74 will provide a base drive via current limiter resistor 84 to the base of voltage modulation transistor 88. A diode 86 is connected between base and ground to prevent back bias of the modulation transistor 88.

When the detected voltage appearing on path 62 is above the threshold level, set by wiper 82 for operational amplifier 74, base drive is obtained which causes voltage modulation transistor 88 to conduct. Resistors 90 and 92 are selected to provide the appropriate gain ratio so as to provide the appropriate change in voltage for the amount of base drive appearing on path 62. As with most feedback circuits there must be some measure of change for the feedback network to act to correct for the change. The output voltage on path 39 to the metastable ionization detector electrode changes in accordance with the changes in the magnitude of the detected current, so as to maintain the current on the path 62 at a substantially constant maximum value. This value is determined by the threshold setting. Although other voltage ranges may be used, in a test model of the control circuit, the voltage applied to MID via path 39 caused the voltage to vary from 450 volts down to about 80 volts as the constituent concentration increased.

Differential amplifier 102 is arranged to accept the differential voltage across resistor 90 as a balanced input so as to minimize any interference from spurious voltages which may otherwise appear in the voltage control circuit. To this end, the sum of resistance values of resistors 90 and 100 is equal to the resistance value of resistor 96, and resistor 104 and 106 are equal valued. At the output of differential amplifier 102 a voltage appears which is representative of the voltage applied to the electrodes of the MID. The output voltage from amplifier 102 is applied via path 108 to a second input of recorder 68. Thus, when the constituent concentration rises above a preset threshold, it is no longer measured by changes in current flowing in the MID. Rather, the constituent concentration is measured by the variations in ionization potential applied to the MID.

The manner in which the modulation voltage automatically increases the operating range of a MID, in accordance with the teachings of this invention, is illustrated by a strip chart recording as represented in the chromatogram of FIG. 3. The modulated voltage metastable ionization detector (MVMID) was operated at 96 degrees, the maximum ionization potential was 510 volts and the bias was set at 0.2 volts. The column or tube was a G.P.B. III-64, 24 feet long by one millimeter in diameter and was operated at 19 degrees Celsius.

To obtain the chromatogram shown in FIG. 3, a sample gas was employed which contained 1002 ppm Argon, 2.1 ppm nitrogen, 1.6 ppm krypton and the balance was the carrier, helium, which had a slight methane contamination. The MVMID was set so that a threshold would occur at about two ppm. As may be seen from the figure, the nitrogen came through the column first in about three minutes, thirty three seconds, and is shown by the peak 110 which rises from the reference current base. Because the concentration of nitrogen in the sample was just slightly above the threshold of two ppm, a small blip 112 is seen on the detector voltage curve. Next in order of appearance was argon (three minutes, 58 seconds), and because of the high concentration of this gas, the change from detector current to detector voltage is seen.

As the presence of the argon gas is first detected, the trace is shown to rise to a peak 114. This peak is the maximum current amplitude that is allowed by MVMID. This peak is above that of peak 110, which is at the threshold level, and peak 114 occurs during the transition from variable current to variable voltage measurement. During this time the modulation voltage becomes operative to reduce the ionization potential on the metastable ionization detector, with the maximum reduction illustrated by the peak 116. Thus, it is seen that the ionization potential is automatically changed so as to accommodate higher concentrations as they occur in the sample under test. By automatically changing the ionization potential as disclosed herein, the operating range is automatically extended for a metastable ionization detector which is operated in conjunction with the modulation voltage technique of the instant invention.

The small current 118 which appears on the chart at the eight minutes and four seconds time is methane, and the krypton appears shortly thereafter, at eight minutes and fifty three seconds. The krypton has a peak 120, and as is shown in the chart it is slightly below the threshold level.

In a concentration gas chromatograph, the concentration of a constituent is a function of the measured detector current, the output current of the metastable ionization detector. In the instant invention, the detector current is used for measurements of low constituent concentration and the variation in detector voltage is employed to measure the higher concentration ranges. The crossover point is adjustable in the circuit because of the use of a variable bias voltage. In operation, it has been observed (with the constituents studied) that there is a non-linear relationship between the measured detector voltage and the concentration of the constituent. Thus, it has been necessary to generate a calibration curve for each constituent.

A dedicated gas chromatographic system was assembled specifically for the development of the MVMID. To simplify the system and minimize possible sources of contamination, a helium ionization detector was removed from a Varian Model 2732 trace gas analyzer, electrically isolated and mounted in a Carle 4300 valve oven. The columns and a Valco gas sampling valve were installed in a separate Carle 4300 valve oven and mated to the detector oven. Both ovens were purged with UHP helium from the carrier and sampling systems. The MID was kept at 100° C., while the column oven temperature ranged from 19° C. to 73° C. depending on the analysis. The remote head of a Keithly 642 electrometer was butted up against the MID oven and connected to the MID. A Keithly 240A high voltage power supply provided the voltage to the MID.

The sample valve was equipped with 100 μl sample loops. An exponential dilution flask (EDF) was used for many of the concentration calibration curves. Samples were injected into the EDF system with a Carle gas sample valve. A Matheson hydrox purifier was used to further clean up the UHP grade helium (Scientific Gas Products, having a minimum purity of 99.999%) that flowed through the EDF system. The hydrox purifier typically removes $O_2$ and $H_2O$.

The carrier gas used was the previously mentioned UHP helium. A hydrox purifier was also installed on the carrier gas system. All connecting lines were 1/16" O.D. 316 stainless steel tubing. The tubing and all fittings were put through an extensive cleaning procedure before being installed in the gas chromatograph.

The Keithly electrometer provided a continuous digital readout of the absolute detector current. A Hewlett-Packard 3469A multimeter was used to measure the detector voltage. Both detector current and detector voltage, at outputs 66 and 108, respectively, were also displayed on a Hewlett-Packard 7100BM strip chart together.

Although the present invention has been described herein in terms of a presently preferred embodiment, it will be appreciated by those skilled in the art that alterations and modifications thereof may be made to suit particular needs and applications. It is therefore intended that the following claims be interpreted as covering all such alterations and modifications as fall within the true spirit and scope of the invention.

What is claimed is:

1. In a gas chromatographic system which employs a carrier gas, and a metastable ionization detector which provides an output signal representative of the concentration of constituents of a substance passing through said system, apparatus for increasing the operating range of said system, which comprises:

power supply means for providing a high voltage ionization potential to said metastable ionization detector; and modulation means responsive to said output signal to maintain the high voltage ionization potential at a maximum amplitude for constituent concentrations below a predetermined threshold level, and to cause the ionization potential amplitude to vary inversely with constituent concentrations as they increase above said threshold level.

2. Apparatus as set forth in claim 1 wherein said modulation means comprises:

differential amplifier means for amplifying the output signals that are representative of the concentration of the constituents of said substance; and means for adjusting said differential amplifier so as to provide a substantially zero output when only the carrier gas is present in the ionization detecting means.

3. Apparatus as set forth in claim 2 wherein said modulation means further comprises:

voltage control means for modulating said high voltage when the constituent concentration is recognized to be above said predetermined threshold level, said voltage control means having a control input and an output;

modulation amplifier means having an input adapted for connection to the output of said differential amplifier and an output adapted for connection to said control input of said voltage control means; and means for setting the gain of said modulation amplifier means so that an output voltage is obtained only when said constituent concentration is higher than said predetermined threshold, said output voltage then being applied to said control input to modulate said high voltage.

4. Apparatus as set forth in claim 3, wherein said voltage control means comprises:

a first resistor having one terminal end adapted for conection to said high voltage output of said power supply means;

a transistor having collector, base and emitter electrodes, said collector electrode being adapted for connection to the other terminal end of said first resistor;

a second resistor having one terminal end connected to said emitter electrode and the other terminal end connected to ground; and said base electrode adapted for connection to said control input, whereby the bias of said transistor is controlled by said modulation amplifier.

5. Apparatus as set forth in claim 4 wherein said modulation amplifier means comprises;

a second differential amplifier having the output of the first said differential amplifier adapted for connection to the non-inverting input thereof, the gain of said second differential amplifier being adjusted so as to provide substantially a zero output until said detecting means output signal represents a constituent concentration that is higher than said predetermined threshold, said second differential amplifier than providing a bias voltage at an output, said bias voltage increasing as the constituent concentration increases above said predetermined threshold;

a third resistor having one terminal end adapted for connection to the output of said second differential amplifier and the other terminal end connected to the base of said transistor, thereby limiting the output current; and a diode having a cathode connected to the base of said transistor and an anode connected to ground, whereby reverse bias of said transistor is prevented.

6. Apparatus for quantitatively analyzing chemical constituents of a sample mixture comprising:

a chromatograph including a tube and employing a gas carrier;

means for inserting a sample of said mixture into said chromatograph, whereby the constituents of said mixture are separated into bands in the gas carrier as it flows through said tube;

means for ionizing the constituents passing in bands through said tube said ionizing means including an ionization voltage input;

power supply means providing a high voltage at an output which is adapted for connection to said ionization voltage input, whereby an ionization field is developed;

means for detecting a change in electrical conductance caused by the presence of the various constituents as developed by said ionization means, and for providing an output signal which is representative of the constituent concentration thereof; and modulation means responsive to said output signal for controlling the amplitude of said high voltage so as to permit a maximum fixed high voltage to be present so long as said constituent concentration is below a predetermined threshold level and to cause the high voltage to vary so as to maintain said output signal substantially constant when the constituent concentration is above said predetermined level.

7. Apparatus as set forth in claim 6 comprising means for recording the variable output signal representative of below threshold constituent concentrations or the variable ionization voltage from said modulation means.

8. Apparatus as set forth in claim 6 wherein said modulation means comprises:

differential amplifier means for amplifying the output signals that are representative of the concentration of the constituents of said substance; and means for adjusting said differential amplifier so as to provide a substantially zero output when only the carrier gas is present in the ionization detecting means.

9. Apparatus as set forth in claim 8 wherein said modulation means further comprises:

voltage control means for modulating said high voltage when the constituent concentration is recognized to be above said predetermined threshold level, said voltage control means having a control input and an output;

modulation amplifier means having an input adapted for connection to the output of said differential amplifier and an output adapted for connection to said control input of said voltage control means; and means for setting the gain of said modulation amplifier means so that an output voltage is obtained when said constituent concentration is above said predetermined threshold and is applied to said control input to modulate said high voltage, and to inhibit said voltage control means when said constituent concentration is below said predetermined threshold.

10. Apparatus as set forth in claim 9 comprising: means for recording; and amplifier means responsive to modulation of said high voltage to provide an input signal to said recording means that is representative of the quantity of the constituents when their concentration is above said predetermined threshold.

11. Apparatus as set forth in claim 9 wherein said voltage control means comprises:

a first resistor having one terminal end adapted for connection to said high voltage output of said power supply means;

a transistor having collector, base and emitter electrodes, said collector electrode being adapted for connection to the other terminal end of said first resistor;

a second resistor having one terminal end connected to said emitter electrode and the other terminal end connected to ground; and said base electrode adapted for connection to said control input, whereby the bias of said transistor is controlled by said modulation amplifier.

12. Apparatus as set forth in claim 11 wherein said modulation amplifier means comprises:

a second differential amplifier having the output of the first said differential amplifier adapted for connection to the non-inverting input thereof, the gain of said second differential amplifier being adjusted so as to provide substantially a zero output until said detecting means output signal represents a constituent concentration that is greater then said predetermined threshold, said second differential amplifier then providing a bias voltage at an output, said bias voltage to increase for detected output signals as they increase above said threshold;

a third resistor having one terminal end adapted for connection to the output of said second differential amplifier and the other terminal end connected to the base of said transistor, thereby limiting the output current; and a diode having a cathode connected to the base of said transistor and an anode connected to ground, whereby reverse bias of said transistor is prevented.

13. Apparatus for quantitatively analyzing chemical constituents of a substance comprising:

a chromatograph including a tube and employing a gas carrier such as helium, hydrogen or nitrogen:

means for inserting a sample of said substance into said chromatograph whereby the constituents are separated into bands interspersed in the gas carrier as it flows through said tube;

means for ionizing the constituents passing through said tube, said ionizing means including an ionization voltage input;

power supply means including a high voltage output adapted for connection to said ionization voltage input, whereby an ionization field is developed;

means for measuring the change in the electrical conductance which results from the concentration of the various constituents as they pass through said ionization means, and for providing an output signal representative thereof;

means for monitoring the change in electrical conductance caused by ionization of said constituents said monitoring means being adapted to permit a fixed high voltage to be applied from said power supply means to the ionization voltage input of said ionization means when the electrical conductance of the constituent concentration is below a predetermined level, whereby the current will vary; and allowing for said high voltage to vary when the electrical conductance is above said predetermined level, said high voltage varying inversely as the electrical conductance whereby the current is held substantially constant; and means for recording the variable parameter.

* * * * *